United States Patent
Neri et al.

(10) Patent No.: US 8,858,485 B2
(45) Date of Patent: Oct. 14, 2014

(54) CONNECTOR FOR A FLUID LINE IN AN EXTRACORPOREAL CIRCUIT

(75) Inventors: Roberto Neri, Mirandola (IT); Andrea Paltrinieri, Mirandola (IT)

(73) Assignee: Gambro Lundia AB, Lund (SE)

( * ) Notice: Subject to any disclaimer, the term of this patent is extended or adjusted under 35 U.S.C. 154(b) by 1295 days.

(21) Appl. No.: 11/100,532

(22) Filed: Apr. 7, 2005

(65) Prior Publication Data
US 2005/0224405 A1   Oct. 13, 2005

Related U.S. Application Data

(60) Provisional application No. 60/522,430, filed on Sep. 30, 2004.

(30) Foreign Application Priority Data

Apr. 13, 2004   (IT) .............................. MO2004A0082

(51) Int. Cl.
*A61M 35/00*   (2006.01)
*A61M 39/18*   (2006.01)
*A61M 1/36*    (2006.01)
*A61M 39/10*   (2006.01)

(52) U.S. Cl.
CPC ............. *A61M 1/3627* (2013.01); *A61M 39/18* (2013.01); *A61M 2039/1061* (2013.01); *A61M 1/3641* (2014.02); *A61M 39/1011* (2013.01); *Y10S 604/905* (2013.01)
USPC .............. 604/4.01; 604/86; 604/88; 604/411; 604/408; 604/409; 604/410; 604/263; 604/414; 604/412; 604/413; 604/244; 604/905

(58) Field of Classification Search
CPC ..... A61M 35/00; A61M 37/00; A61M 25/00; A61M 5/32; A61M 5/00; A61M 19/00; A61M 9/22
USPC ..................... 604/4.01, 86, 88, 411, 408–410
See application file for complete search history.

(56) References Cited

U.S. PATENT DOCUMENTS 4,443,219 A * 4/1984 Meisch et al. ................ 604/317
4,508,367 A   4/1985 Oreopoulos et al.
(Continued)

FOREIGN PATENT DOCUMENTS

DE  4000873   7/1991
DE  4220831   4/1994
(Continued)

OTHER PUBLICATIONS

The American Heritage® Dictionary of the English Language, Fourth Edition, 2000.*

*Primary Examiner* — Tatyana Zalukaeva
*Assistant Examiner* — Ilya Treyger
(74) *Attorney, Agent, or Firm* — Novak Druce Connolly Bove + Quigg$^{LLP}$

(57) ABSTRACT

The connector for a fluid line of an extracorporeal circuit comprises a tubular body which internally defines a fluid passage, a first connection port predisposed for coupling to the fluid line, a second connection port predisposed for coupling to a male Luer connector borne by an external element, and a closure element of the second connection port. The closure element is formed of a breakable membrane made in a single piece with the tubular body. On coupling, the membrane is broken by the truncoconical projection of the male Luer connector. The connector connects a service line of an extracorporeal circuit to a pressure sensor of a dialysis machine.

62 Claims, 8 Drawing Sheets

(56) References Cited

U.S. PATENT DOCUMENTS

| | | | |
|---|---|---|---|
| 4,673,400 A | | 6/1987 | Martin |
| 4,681,606 A | * | 7/1987 | Swan et al. ............... 96/197 |
| 4,731,058 A | | 3/1988 | Doan |
| 5,242,408 A | | 9/1993 | Jhuboo et al. |
| 5,295,967 A | | 3/1994 | Rondelet et al. |
| 5,501,665 A | | 3/1996 | Jhuboo et al. |
| 5,520,640 A | * | 5/1996 | Utterberg ............... 604/80 |
| 5,647,853 A | | 7/1997 | Feldmann et al. |
| 5,919,146 A | * | 7/1999 | Propp ............... 600/577 |
| 5,983,947 A | | 11/1999 | Utterberg |
| 6,200,289 B1 | | 3/2001 | Hochman et al. |
| 6,234,538 B1 | | 5/2001 | Lauer |
| 6,269,340 B1 | | 7/2001 | Ford et al. |
| 6,423,035 B1 | | 7/2002 | Das et al. |
| 2001/0034502 A1 | | 10/2001 | Moberg et al. |
| 2002/0128594 A1 | | 9/2002 | Das et al. |
| 2004/0015124 A1 | | 1/2004 | Sciulli et al. |
| 2004/0133166 A1 | | 7/2004 | Moberg et al. |

FOREIGN PATENT DOCUMENTS

| | | | |
|---|---|---|---|
| DE | 19617024 | * | 6/1997 |
| DE | 19617024 | * | 11/1997 |
| EP | 0 278 146 | | 8/1988 |
| EP | 0 319 648 | | 6/1989 |
| EP | 0 402 553 | | 12/1990 |
| EP | 0 589 328 | | 3/1994 |
| EP | 0803267 | | 10/1997 |
| EP | 0 916 353 | | 5/1999 |
| EP | 1 066 846 | | 1/2001 |
| EP | 1 188 454 | | 3/2002 |
| EP | 1 362 606 | | 11/2003 |
| FR | 2 757 772 | | 7/1998 |
| GB | 2 224 444 | | 5/1990 |
| GB | 2 356 349 | | 5/2001 |
| WO | WO 03/077826 A2 | | 9/2003 |

* cited by examiner

CONNECTOR FOR A FLUID LINE IN AN EXTRACORPOREAL CIRCUIT

CROSS-REFERENCE TO RELATED APPLICATIONS

This application claims the benefit of priority of U.S. provisional application No. 60/522,430, filed on Sep. 30, 2004, and Italian patent application no. MO2004A000082, filed on Apr. 13, 2004, both of which are incorporated herein by reference in their entirety.

BACKGROUND OF THE INVENTION

The invention relates to a connector for a fluid line of an extracorporeal circuit, to a use for a connector for a fluid line of an extracorporeal circuit, to an extracorporeal blood circuit, to an apparatus for extracorporeal blood treatment, and to a process for manufacturing a connector for a fluid line of an extracorporeal circuit.

Specifically, though not exclusively, the invention can be usefully applied in the field of extracorporeal treatment for kidney failure, for example for connecting an extracorporeal blood circuit to a pressure sensor of a dialysis machine.

The prior art comprises a blood chamber for an extracorporeal circuit realised according to the preamble of the first claim, in which a service line has a first end connected to the blood chamber and a second end predisposed for connection to an external element (for example a pressure sensor of a machine for extracorporeal blood treatment). The second end exhibits an opening which, in an operating configuration, at least partially receives a projection (for example, the projection of a male Luer connection) provided on the external element. Before use, the second end of the service line is normally closed, for hygienic and security reasons, by a closure element usually constituted by a plug connected removably to the second end, for example by means of a sealed fluid-proof screw coupling of the Luer type.

The closure elements, used in the prior art to keep the fluid lines of an extracorporeal circuit closed, exhibit some drawbacks and lacks.

Firstly, the closure element has to be manufactured separately from the service line assembled thereon subsequently, with a consequent increase in costs and times of production of the extracorporeal circuit.

Secondly, the closure element must be removed from the service line before use, increasing complications in the already-complex various phases of readying the extracorporeal circuit on the machine performing the extracorporeal treatment.

Thirdly, the closure element might be removed before it should be, for example by error on the part of the operator, with the risk of contamination of the service line and the treatment machine the line is to be associated to.

Furthermore, the known-type closure element, being easily reclosable, is unable to signal a first opening, i.e. it cannot guarantee that the fluid line, apparently closed up until the moment of its use, has not been previously opened with a consequent risk of external contamination.

SUMMARY OF THE INVENTION

An aim of the present invention is to provide a blood chamber, in particular for an extracorporeal blood circuit, which does not exhibit the limitations and drawbacks of the prior art.

A further aim of the invention is to provide a connector which is constructionally simple and economical, which is associated to an end of a fluid line of an extracorporeal circuit, and which is usable for connecting the fluid line to an external element, such as for example a device associated to a machine for extracorporeal blood treatment. In particular, the fluid line can comprise a service line or auxiliary line, i.e. not destined to be used by the blood flow, which is fluidly connected to a blood chamber on one side and connectable to a machine for extracorporeal blood treatment on the opposite side. The fluid line can comprise other parts of an extracorporeal circuit, such as for example the arterial or venous line of the circuit, in which case the connector can advantageously be used for rapid connection of the fluid line to a device for vascular access (arterial and/or venous), or to a device for extracorporeal blood treatment (for example a dialyzer).

A further aim of the invention is to make available a simple and economical process for manufacturing the above-described connector.

An advantage of the invention is that it reduces costs and times of production of the extracorporeal circuit.

A further advantage is that it simplifies the readying operations of the extracorporeal circuit on the machine which carries out the extracorporeal treatment.

A further advantage is that it reduces the risk of contamination of the extracorporeal circuit.

A still further advantage is that any first opening of the fluid line of the extracorporeal circuit can be verified.

Furthermore the invention reduces the risk that a service line in the extracorporeal circuit, having a closed end destined to be opened immediately before coupling with a machine for extracorporeal treatment, can be opened—inadvertently or intentionally—before it should.

These aims and advantages and more besides are all attained by the present invention, as it is characterised by one or more of the appended claims.

According to an embodiment of the invention, the closure element of the connection port is openable by effect of a force exerted from the outside towards the inside of the connection port.

By virtue of this feature the opening of the fluid line is performed at the time of its fluid connection with the external element, with a consequent simplification of the readying procedure of the apparatus for extracorporeal blood treatment.

The above-mentioned feature of the openable element towards the inside can be obtained in various ways: for example, by use of a closure element having a breakable part (as in the examples illustrated in the detailed description that follows); or by use of a valve closure element, with a normally closed mobile obturator which is openable towards the inside of the connection port; or by use of an elastically-deformable sealing element (pre-perforated or not) which can be penetrated by an element entering the connection port; and so on.

In the case of a penetrable closure element, whose opening is brought about by an external element penetrating the connection port and also penetrating the sealing material of which the closure element is made, a part of the element opens towards the inside, and deforms (either elastically or not) by effect of the insertion of the external element into the connection port.

In an embodiment of the invention, the closure element is openable by rotating at least a part thereof about a hinge. The hinge can be, for example, fashioned at a zone of greater thickness close to an internal surface of the connection port.

In an embodiment of the invention, the closure element comprises a breakable body which exhibits at least one easy-break zone. An element realised in this way provides a visual signal of a first-time opening. In a special case the above-mentioned body can be constrained on the perimeter of the connection port and can have a central zone, weakened by a gradual thinning thereof towards the centre. In another case, the predetermined easy-break zone can be formed by one or more weakened score-lines, such as for example a plurality of weakened lines arranged spoke-fashion departing from a central zone. In the special cases described above, the shape and arrangement of the structurally weakened zones guarantees in all cases a fluid seal in the closed configuration, facilitates the moulding of the closure element and further eases the opening phase, achieved by an inwardly-directed rupture.

In an embodiment of the invention, the closure element is a membrane arranged transversally with respect to an axis of the connection port.

In an embodiment of the invention, the closure element is realised in a single piece with a tubular connector arranged on the end on the fluid line destined for coupling to the external element.

In an embodiment of the invention, the closure element is realised in the same material (for example a plastic material) as the tubular connector associated to the fluid line and is destined to be coupled to the external element.

In an embodiment of the invention, the closure element is solidly connected along a perimeter thereof to the connection port.

In an embodiment of the invention, the connection line comprises a flexible tube having, at an end thereof, a tubular connector which bears the closure element.

In an embodiment of the invention, the closure element is structured and arranged in order to be opened towards the inside of the connection port by breakage performed by a projection of an external element which enters the connection port. This projection can be, for example, a trunco-conical element of a male Luer connector.

In an embodiment of the invention, the closure element is situated at a certain distance from an end opening of the connection port, for example at a distance which is less than double the diameter of the opening. In an embodiment of the invention, the distance is also less than the difference between the length of the projection of the external element which enters the connection port and the diameter of the closure element, so that in an open configuration the projection can completely cover the closure element; in this case, in the open configuration (see FIG. 8) the closure element is positioned and squeezed between the projection of the external element and the internal wall of the connection port, and is not interested by the passage of fluid.

In an embodiment of the invention, the closure element is situated at a certain distance from an end opening of the connection port, for example at a distance greater than half of the diameter of the end opening.

In an embodiment of the invention, in which the closure element is situated at a certain distance from the end opening of the connection port, the connection port exhibits a seal zone, comprised between the closure element and the end opening, with a converging direction in an inwards direction. The seal zone, which can have a transversal section which converges inwardly (for example trunco-conical), collaborates to ensure the fluid seal once the coupling has been achieved.

In an embodiment of the invention, the fluid connection line is a service line not destined to have blood flow through it.

In an embodiment of the invention, a tubular connector for a fluid line of an extracorporeal circuit is provided with a closure element that is openable in an internal direction, in particular by effect of a contact thrust exerted by a solid body inserted in an opening of the connector itself.

In an embodiment of the invention, the tubular connector internally defines a fluid passage, with a straight axis, open at the opposite ends and completely closed laterally.

In an embodiment of the invention, a tubular connector for a fluid line of an extracorporeal circuit is manufactured by injection moulding of a plastic material to make a single tubular body made up of two connection ports, oppositely situated, and a breakable body arranged transversally to close a fluid passage afforded between the two connection ports.

Further characteristics and advantages of the present invention will better emerge from the detailed description that follows, of at least one preferred embodiment of the invention, illustrated by way of non-limiting example in the figures of the drawings.

BRIEF DESCRIPTION OF THE DRAWINGS

The description will be made herein below with reference to the accompanying figures of the drawings, provided by way of non-limiting illustration, and in which.

DETAILED DESCRIPTION

Figure 1:
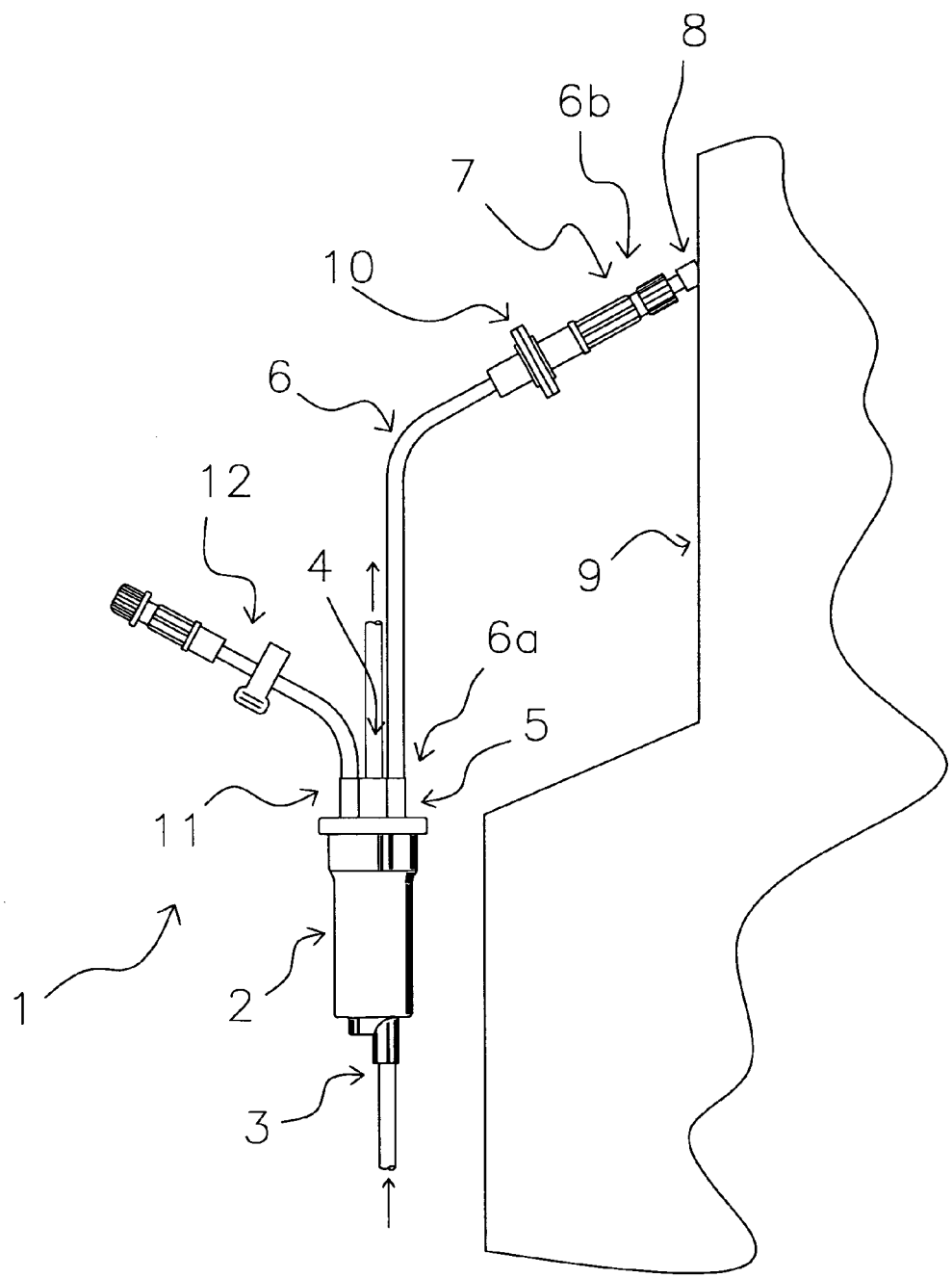
FIG. 1 is a partial view in vertical elevation of an extracorporeal blood circuit associated operatively to a machine for performing an extracorporeal blood treatment.
Figure 2:
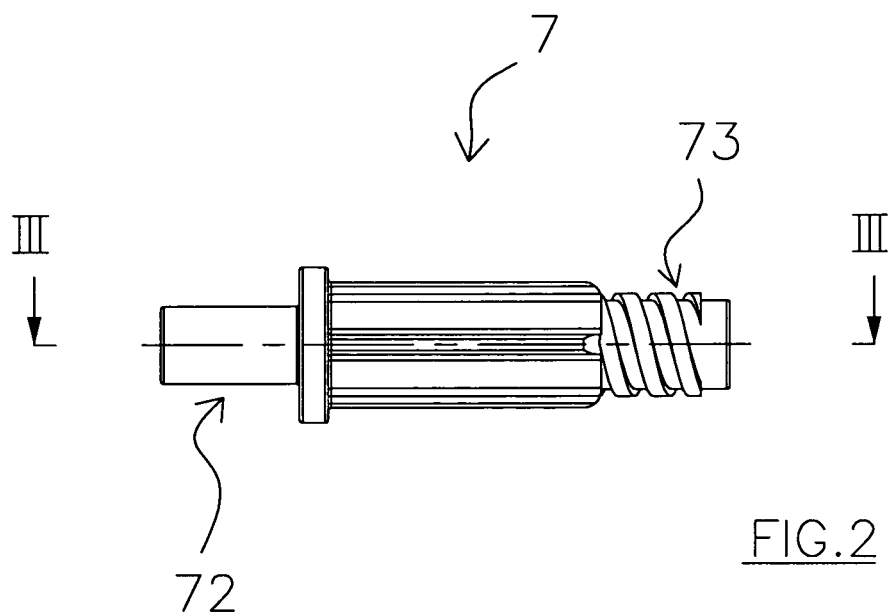
FIG. 2 is an enlarged lateral view of the end connector of the auxiliary line of the extracorporeal circuit which, in FIG. 1, is coupled to a seating associated to the front panel of the machine.
Figure 3:
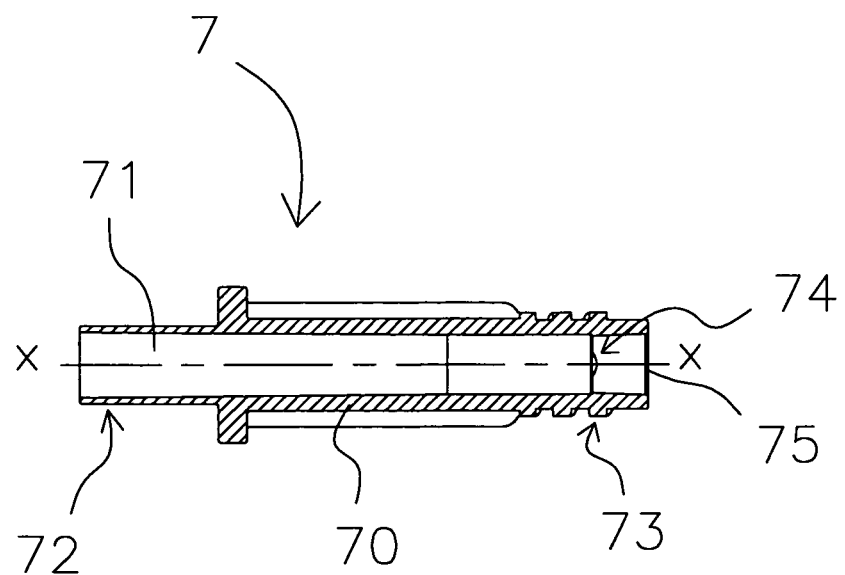
FIG. 3 is a section made according to line III-III of FIG. 2.
Figure 4:
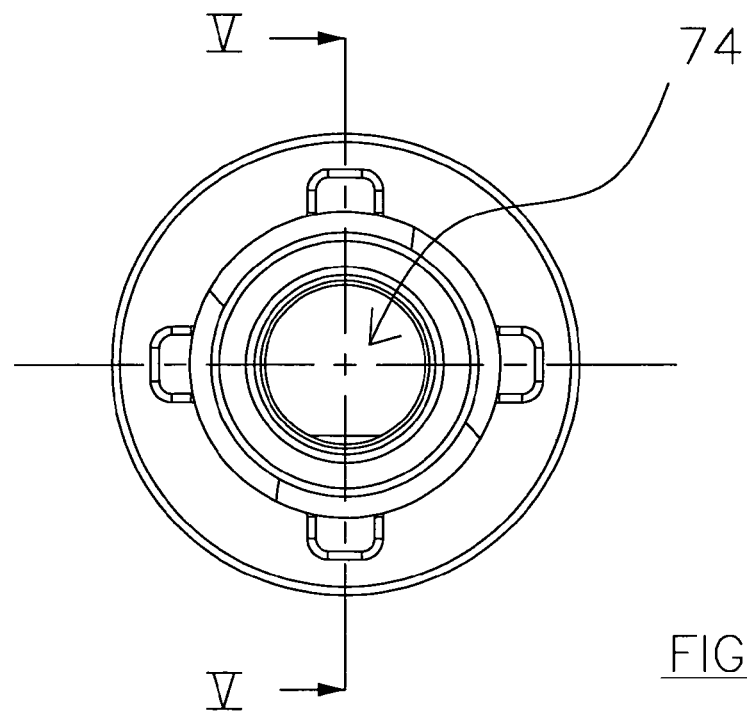
FIG. 4 is an enlarged view from the right of FIG. 2.
Figure 5:
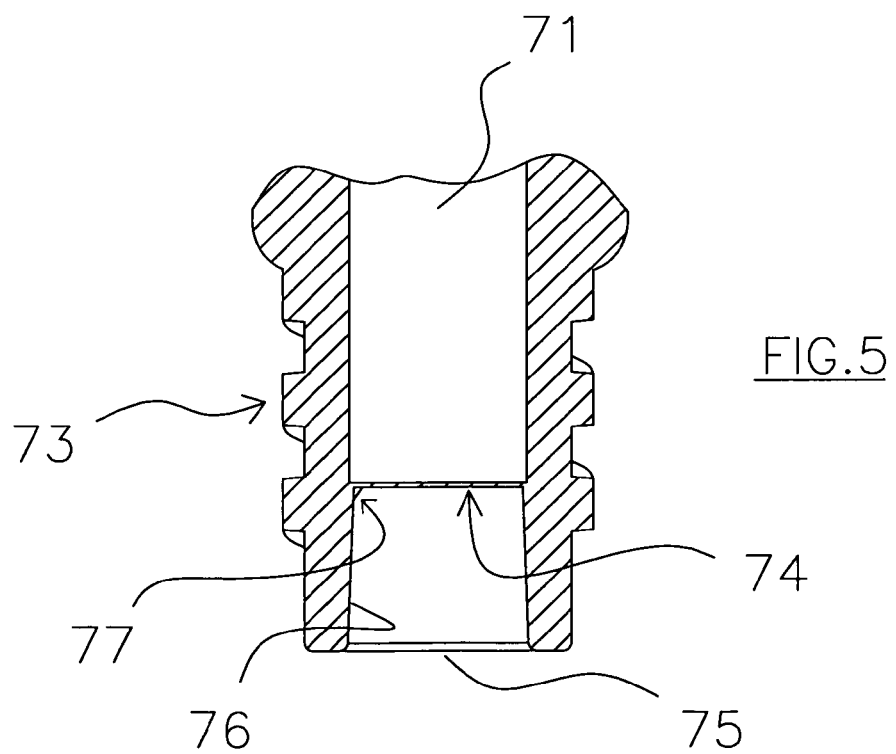
FIG. 5 is an interrupted section of line V-V of FIG. 4.
Figure 6:
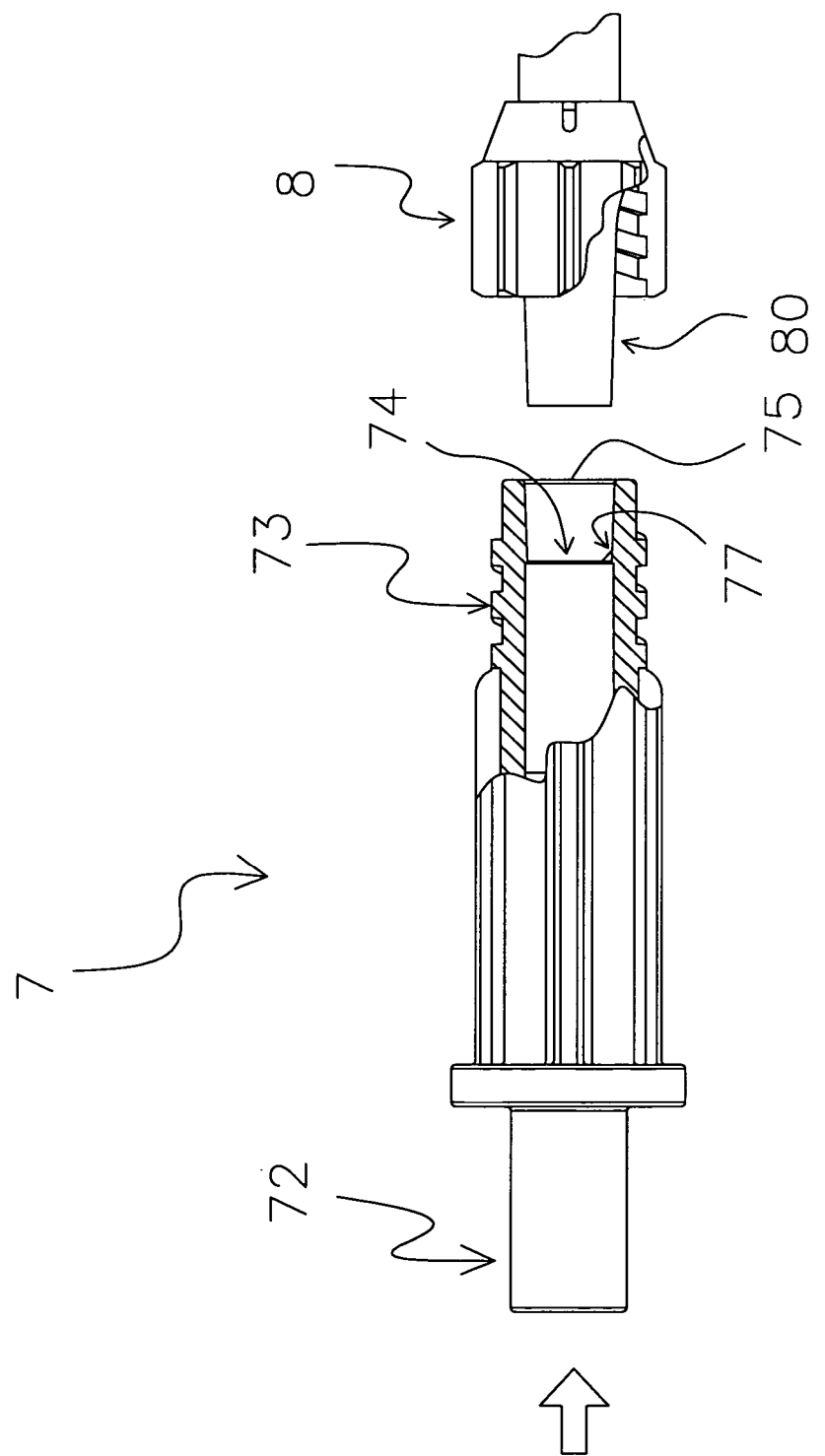
FIGS. 6 to 8 show three different stages of the coupling of the connector, associated to the auxiliary line, and the seating, associated to the machine, visible in FIG. 1.
Figure 7:
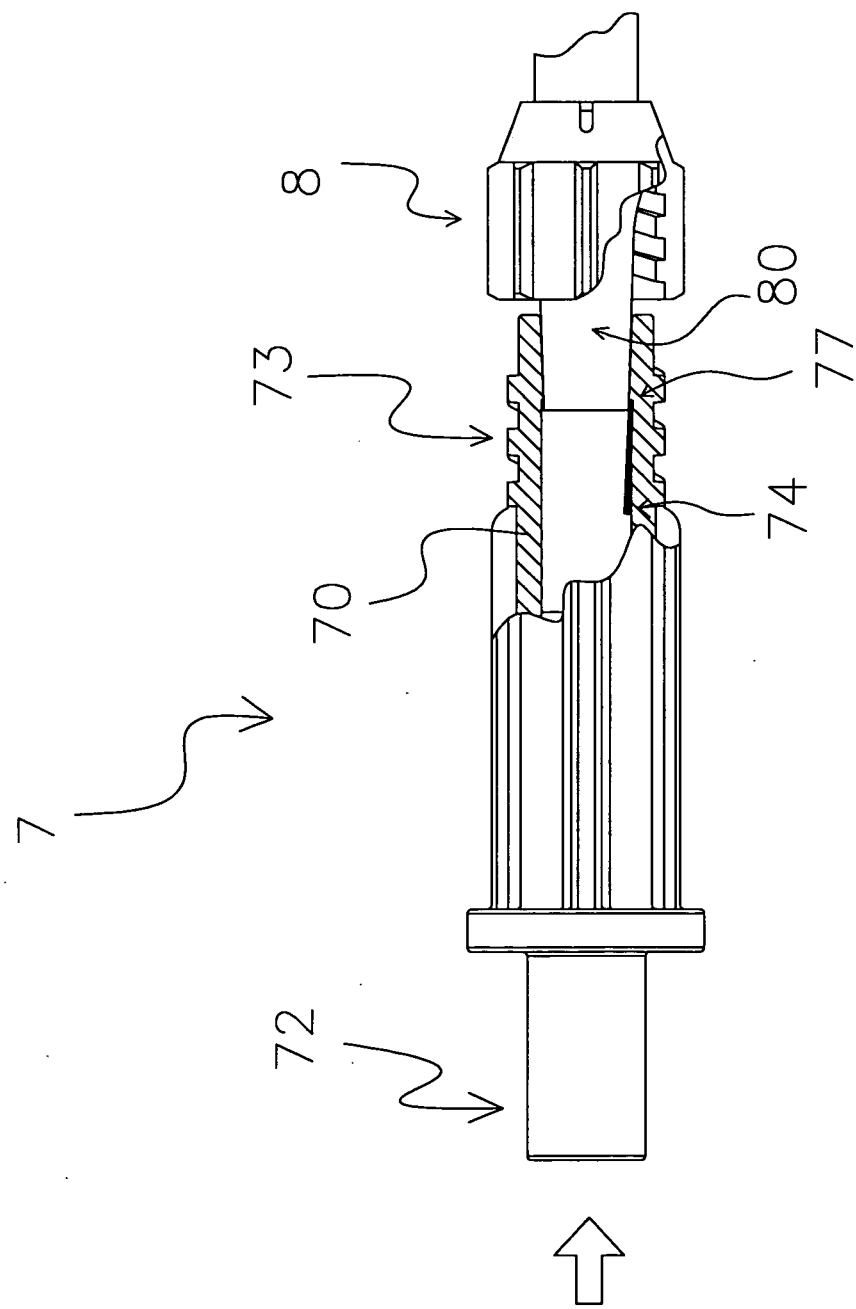
Figure 8:
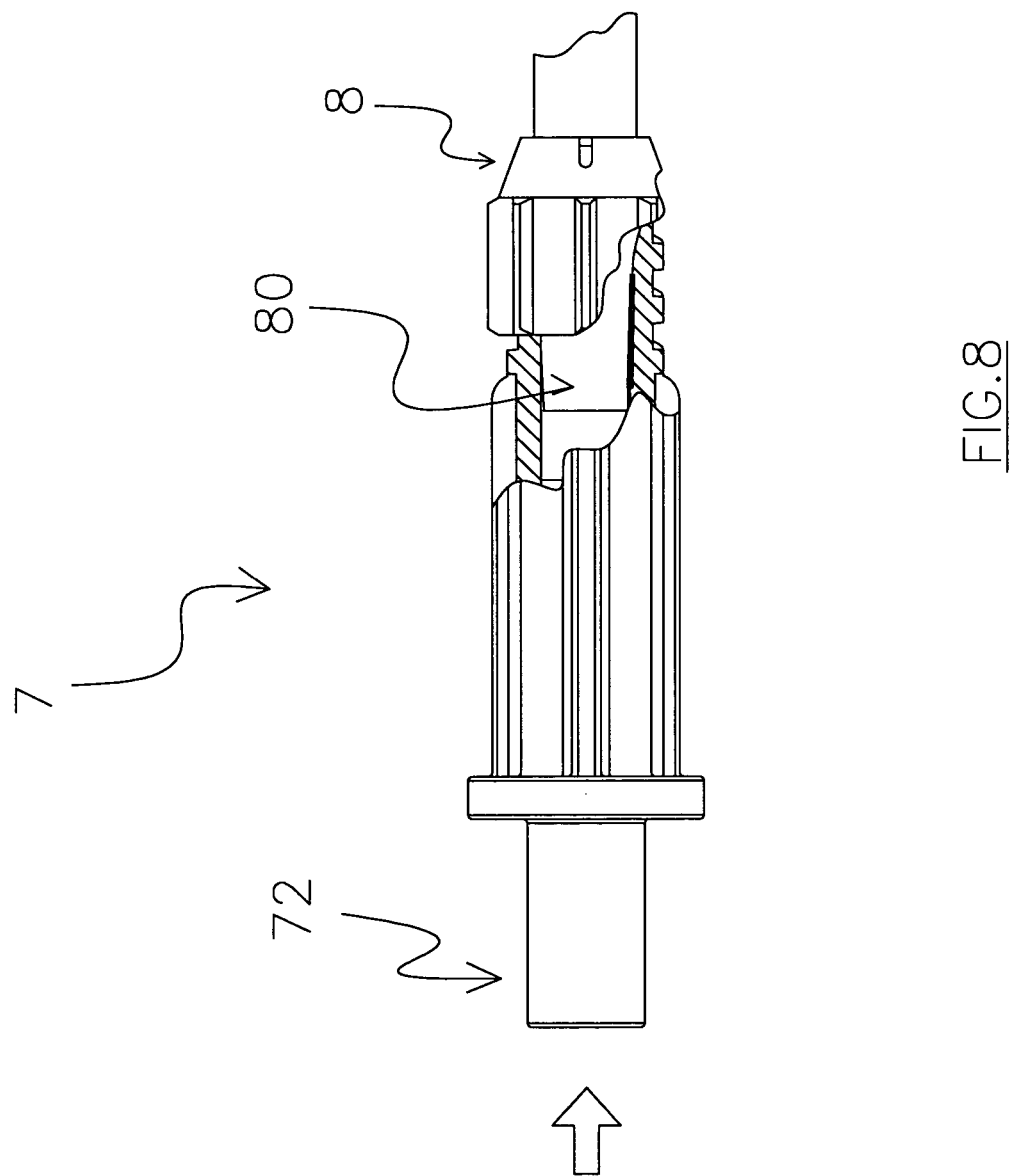

With reference to FIGS. 1 to 8, 1 denotes in its entirety an extracorporeal blood circuit. In the specific embodiment in FIG. 1 a part of the circuit is illustrated, comprising a blood chamber 2 provided with a blood inlet port 3 and a blood outlet port 4. The extracorporeal circuit further comprises various other parts (for example tubes, access sites for removal and/or injection, sites for measuring circuit parameters, connectors, clamps, etc.) which are of known type and which are therefore not described in detail.

The blood chamber 2 further comprises an auxiliary port for fluid access, i.e. a service port 5, and an auxiliary fluid connection line 6, i.e. a service line, for connection with an external element. The service line, which is not destined to be used by the main blood flow, has a first end 6a which is connected to the auxiliary port 5, and a second end 6b, opposite the first end 6a, which has a connector 7 connected to a seating 8 associated to a front panel 9 of a machine for extracorporeal blood treatment.

In particular, the service line comprises a flexible tube running between the first end 6a and the second end 6b. The connector 7 is solidly connected to the flexible tube.

The machine can be, for example, suitable for performing one or more of the following treatments: hemodialysis, hemofiltration, hemodiafiltration, pure ultrafiltration, plasmapheresis.

The seating 8 on the machine is fluidly connected to a pressure sensor (of known type and not illustrated), which sensor is also associated to the machine, in order to provide the machine processor with signals correlated to the real value of the pressure in the blood chamber 2.

The service line is provided with a transducer-protector device 10, of known type, provided with an anti-contamination barrier which is gas-permeable, in order to prevent passage of contaminating agents and to enable, at the same time, a reading of the pressure in the blood chamber 2 by the pressure sensor associated to the machine.

The blood chamber 2 is provided, in the specific embodiment, with a second service port 11, usable for connection to a second service line 12, such as for example a line for regulating a level of blood internally of the chamber 2.

The connector 7, which is illustrated in greater detail in FIGS. 2 to 5, comprises a tubular body 70 which internally defines a fluid passage 71. The fluid passage 71 has, in the specific embodiment, a straight axis x-x.

The tubular body 70 has a first connection port 72, predisposed for coupling with a service line, in order to create a fluid communication (essentially an air passage) between the line 6 and the passage 71. In the specific embodiment the first connection port 72 is provided for fluidly sealed coupling with the transducer-protector device 10.

The tubular body 70 has a second connection port 73, coaxial to and opposite the first port 72, which is predisposed for coupling with the seating 8. In the specific embodiment, the second connection port 73 exhibits a female Luer connection, while the seating 8 has a male Luer connection. The seating 8 is therefore provided with a projection 80, externally truncoconical, which in a coupled configuration (FIG. 8) is destined at least partially to enter an opening 75 of the second connection port 73.

The tubular body 70 is further provided with an obturator, or a closure element 74 for fluidly sealed closure. The obturator 74 is openable towards the inside by effect of insertion of the projection 80 in the opening 75, as can clearly be seen in FIGS. 6 to 8.

When the obturator 74 is opened, a fluid connection can be established between the blood chamber 2 and the machine pressure sensor, through the service line.

In general, the obturator 74 is openable by a direct push from the outside towards the inside of the second connection port 73.

In the illustrated embodiment, the obturator 74 comprises a breakable body, in the form of a membrane, which is transversally arranged in order to obstruct the fluid passage 71. The obturator 74 is made in a single piece by injection moulding of plastic material with the tubular body 70.

The obturator 74 is arranged internally of the cavity of the tubular body 70 which forms the fluid passage 71, and is situated at a predetermined distance from the end opening 75. An internal surface 76 is predisposed between the obturator 74 and the opening 75, which internal surface 76 defines a passage with a decreasing transversal section in an internal-wise direction, going from the opening 75 towards the obturator 74. The internal surface 76 is, in the illustrated embodiment, truncoconical with a predetermined conicity and is a sealing surface of the female Luer connection.

The obturator 74 is provided with a hinge 77; at least a part of the obturator 74 can assume at least one open configuration (FIGS. 7 and 8) in which, with respect to a closed configuration (FIG. 6) it is rotated about the hinge 77.

The hinge 77 is fixed to an internal surface of the second connection port 73. In the illustrated embodiment the hinge 77 comprises a thickened part of the membrane forming the obturator 74. In an open configuration (FIG. 8), the closure element 74 is squeezed between the projection 80 and the lateral wall of the second connection port 73, and is completely covered by the projection.

A perimeter of the obturator 74 is solidly connected to an internal surface of a wall of the second connection port 73.

The breakable body forming the obturator 74 can exhibit an easy-break zone, for example circumferential extending along the perimeter.

As previously mentioned, the second connection port 74 exhibits an end opening 75 which, in a configuration of connection with the seating 8, at least partially receives the projection 80 of the seating 8. The projection 80 has a truncoconical external surface for fluidly-sealed coupling with the internal surface 76 on the connector 7. The projection 80 is responsible for the contact thrust against the obturator 74 which thrust causes the fluid passage 71 to open, at the moment of coupling between the connector 7 and the seating 8.

The projection 80 is responsible for the contact thrust against the obturator 74 which determines the opening of the fluid passage 71, on the coupling of the connector and the seating 8.

The obturator 74 is situated at an axial distance comprised between about half and about double the diameter of the opening 75. In the embodiment this distance is about the same as the diameter.

The axial distance from the opening 75 enables the obturator 74 to be placed in contact with the projection 80 on insertion thereof, and also makes possible a seal zone, in a converging section towards the inside, located internally of the second connection port 73 between the obturator 74 and the opening 75.

Figure 9:
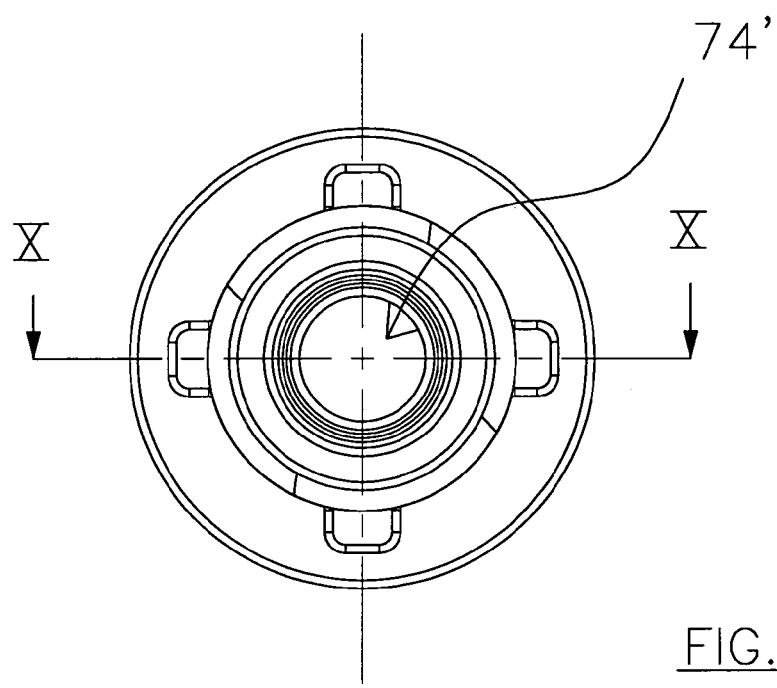
FIG. 9 is a front view, as in FIG. 4, of a second embodiment of a connector made according to the invention.
Figure 10:
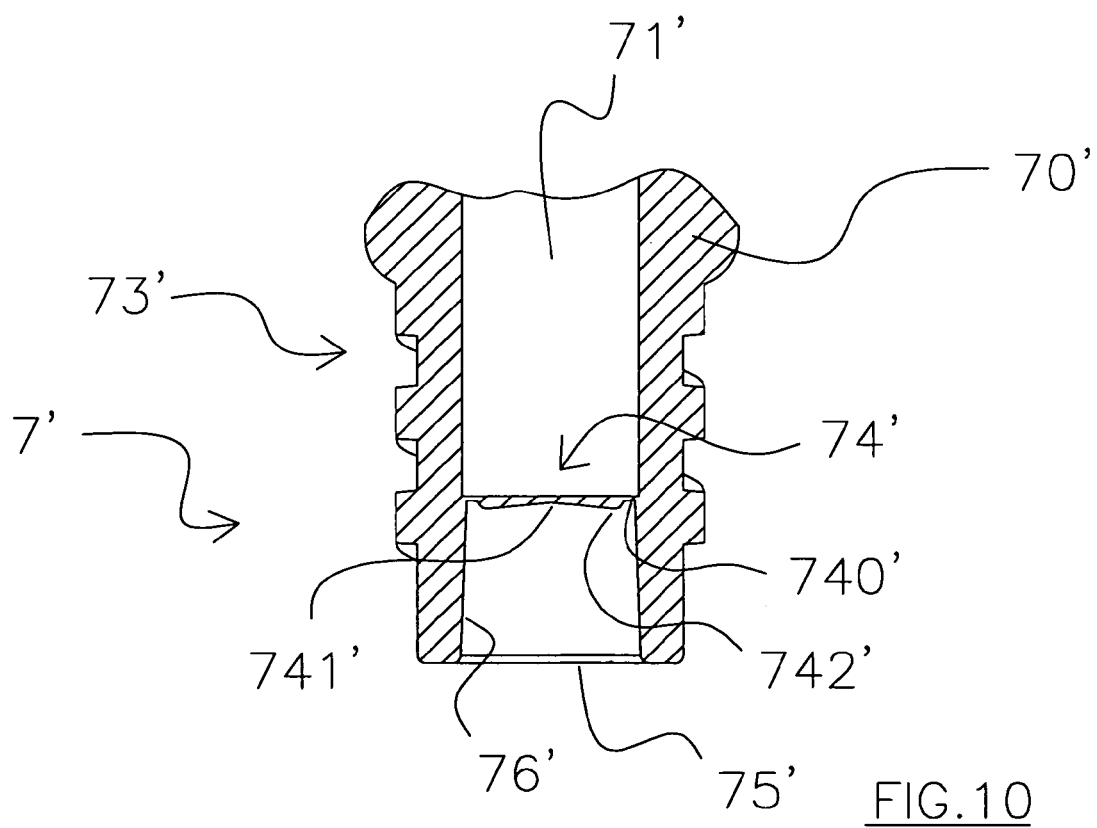
FIG. 10 is an interrupted section of line X-X of FIG. 9.

In the illustrated embodiment of FIGS. 9 and 10, which only display the second connection port 73'—the rest being the same as what has already been described—the tubular connector 7' comprises an obturator 74', also of a breakable type, having a perimeter part 740' which is constrained to the internal surface of the tubular body 70', and a central part 741' having a breadth that diminishes going from the periphery towards the centre. The perimeter part 740', which has a smaller thickness, surrounds a high-thickness intermediate annular projection 742', which in turn surrounds the larger central part 741', which thins gradually down towards the centre.

The obturator 74', thanks to its conformation, can be easily moulded by injection of plastic material and is solidly anchored to the tubular body 70', effectively sealedly closing it, and is easily openable by effect of insertion of the truncoconical projection 80 of the male Luer connector.

Figure 11:
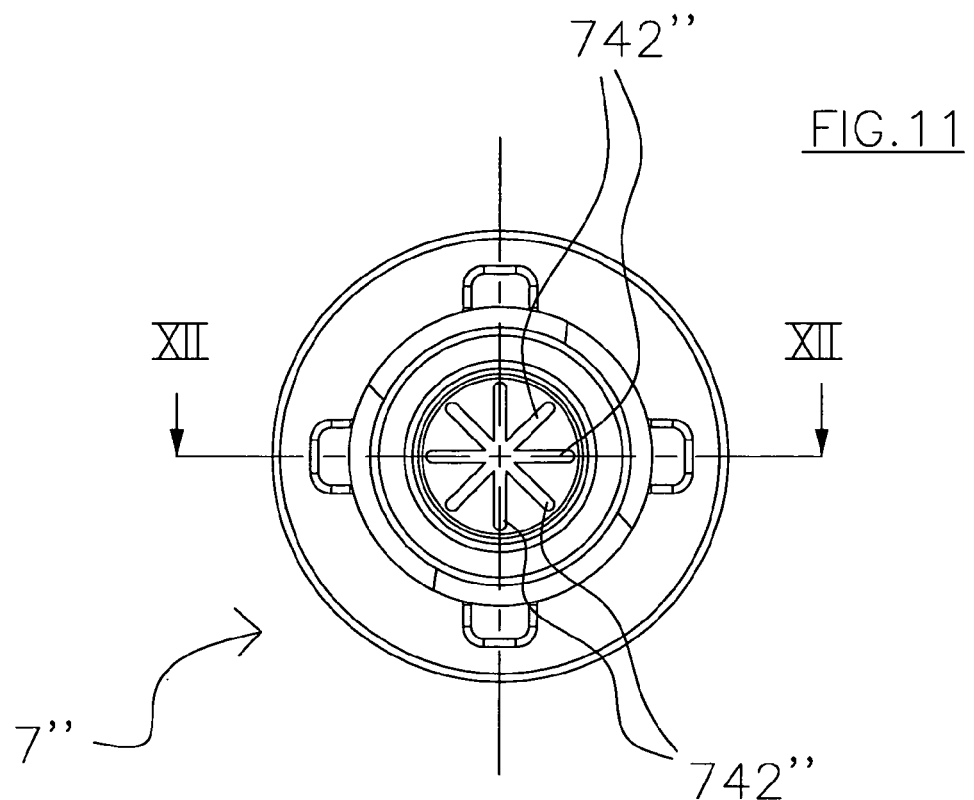
FIG. 11 is a front view, as in FIGS. 4 and 9, of a third embodiment of a connector made according to the present invention.
Figure 12:
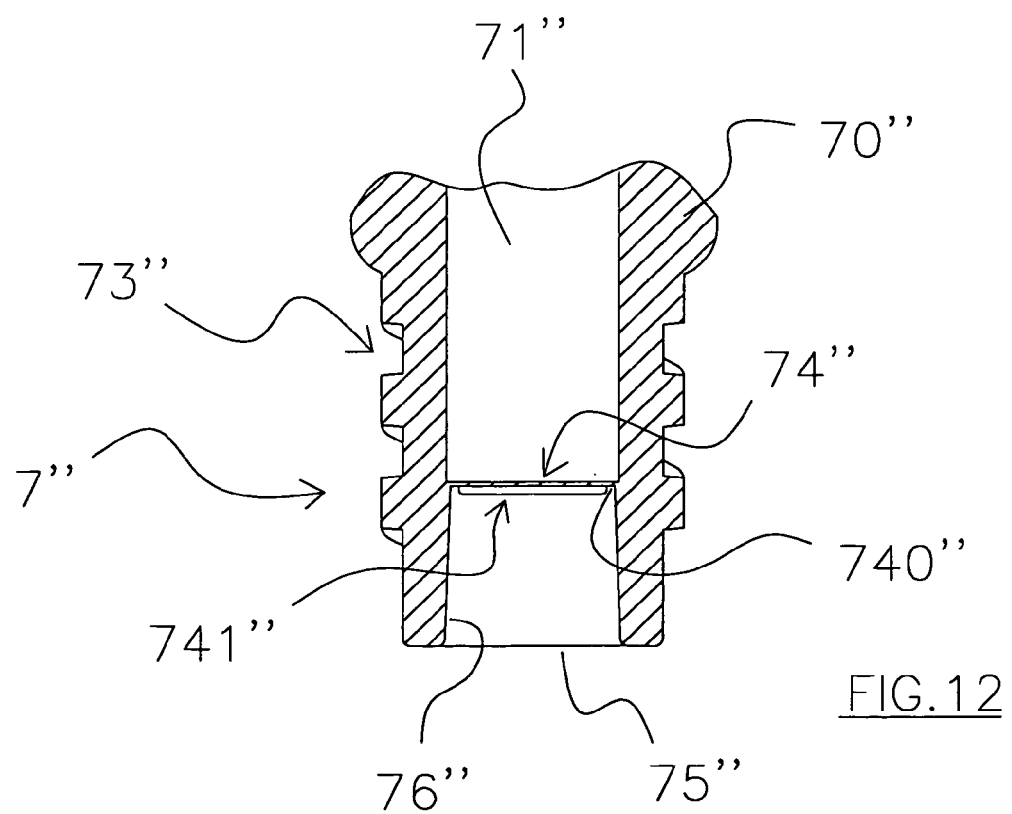
FIG. 12 is an interrupted section of line XII-XII of FIG. 11.

In the version illustrated in FIGS. 11 and 12, the obturator 74" comprises a breakable membrane with a perimeter part 740" having a smaller thickness, constrained to the second connection port 73", and an internal part 741" which exhibits a plurality of weakened lines 742" arranged spoke-fashion departing from a central zone of the membrane.

In the above-illustrated examples a fluid line is described which on a connection port is provided with a normally-closed obturator which is openable by giving way following an action exerted towards the inside of the port. The fluid line has been described as a line performing the function of a service line, in particular for detecting the pressure in the extracorporeal circuit. It is however possible that the obturator, or other closure element openable by effect of a coupling element insertable in the connection port, may be associated to a fluid line performing other functions: for example, a fluid transport line for the main blood flow, or an auxiliary line for injection of a liquid to be infused into the blood, or an auxiliary line for obtaining samples of blood from the circuit, and so on.

The obturator, which in the given examples is breakable, can be of another type: for example it can be mobile with elastic positioning in the closure position, or it can be of a type which seals but which can be penetrated by a solid body exerting a penetrating thrust, or of another type.

In other words, the obturator can be, or can comprise, an element that closes an access port by detachment, by rotation, by penetration, by laceration, etc., by effect of a body entering the access port, or in any case, by effect of a thrusting action directed towards the inside and exerted by means that are solid, liquid or gaseous.

In an embodiment that is not illustrated, an extracorporeal blood circuit comprises a plurality of fluid lines, at least one of which is provided with a tubular connector such as the ones described herein above. In particular the circuit comprises: an arterial line, or a blood removal line, having at least a first end which is destined to be connected with a vascular access device, and at least a second end destined to be connected to a blood treatment device; a venous line, or a blood return line, having at least a first end which is destined to be connected to a blood treatment device, and at least a second end destined to be connected to a vascular access device; one or more service lines, each having at least a first end fluidly connected to a blood pathway in the circuit, and at least a second end destined to be fluidly connected with an external element.

The connector can be used on one or more of the ends of the above-described fluid lines. In particular the connector can be used to connect the arterial line with the vascular access device, and/or with the blood treatment device; the connector can also be used to connect the venous line with the blood treatment device, and/or with the vascular access device; the connector can also be used for connection of a fluid line with a collection bag for the extracorporeal circuit priming liquid; in these cases the connector can be associated directly to the bag, for example to an edge of the bag, or it can be associated to an end of a fluid transport line having an opposite end in communication with the bag.

The first connection port 72 of the connector can be used for sealed connection with a tube, with a device associated to the circuit (for example the transducer-protector device 10), with a bag or with any other element which can contain and/or transport a fluid.

The invention claimed is:

1. A connector for a fluid line of an extracorporeal circuit, comprising a tubular body which internally defines a fluid passage, said tubular body having:
    at least a first connection port predisposed for coupling with said fluid line;
    at least a second connection port configured to rotatably couple with a projection of an external element; and
    at least a closure element of said second connection port, said closure element being openable towards an inside of said second connection port, said closure element having an open configuration wherein the closure element is positioned and squeezed between the projection of the external element and an internal lateral wall of the second connection port and is completely covered by the projection.

2. A blood chamber for an extracorporeal circuit comprising:
    the connector of claim 1;
    at least one access port; and
    at least one connection line having a first end connected to said at least one access port and a second end connected with said first connection port.

3. The chamber of claim 2, wherein said closure element is provided with at least one hinge, at least a part of said closure element being able to assume an open configuration in which, with respect to a closed configuration thereof, said at least a part of the closure element is rotated about said at least one hinge.

4. The chamber of claim 3, wherein said hinge comprises a localised thickened part of said closure element.

5. The chamber of claim 2, wherein said closure element comprises a breakable body.

6. The chamber of claim 5, wherein said breakable body exhibits at least one zone predisposed for easier breakage.

7. The chamber of claim 6, wherein said zone predisposed for easier breakage comprises one or more weakened lines.

8. The chamber of claim 7, wherein said zone predisposed for easier breakage comprises a plurality of weakened lines arranged in a spoke-fashion departing from a central zone of said breakable body.

9. The chamber of claim 5, wherein said breakable body has a perimeter part which is constrained to said connection port, and a central part which gradually becomes thinner in a direction towards a centre of said breakable body.

10. The chamber of claim 2, wherein said closure element is a membrane which transversally occludes said connection port.

11. The chamber of claim 2, wherein said connection port is associated to a tubular connector and wherein said closure element is realised in a single piece with said tubular connector.

12. The chamber of claim 2, wherein said connection line defines a main fluid pathway which develops between said first end and said second end, said main fluid pathway being interrupted by said closure element.

13. The chamber of claim 2, wherein said closure element is at least partially openable in an opening direction which is parallel to or which coincides with a longitudinal axis of a main fluid pathway defined by said connection line.

14. The chamber of claim 2, wherein said closure element is arranged transversally with respect to a longitudinal axis of a main fluid pathway defined by said connection line between said first end and said second end.

15. The chamber of claim 2, wherein said connection port is located on a tubular connector made of a plastic material, and wherein said closure element is made of a same material as said tubular connector.

16. The chamber of claim 2, wherein said closure element has a perimeter which is solidly connected to a wall of said connection port.

17. The chamber of claim 2, wherein said connection line comprises a flexible tube, extended between said first end and said second end, and a tubular connector connected to said flexible tube at said second end, said closure element being located on said tubular connector.

18. The chamber of claim 2, wherein said connection port exhibits an end opening which is predisposed, in a configuration of connection with said closure element, at least partially to receive a projection exhibited on said external element, said closure element being openable by effect of a contact thrust exerted by said projection during insertion thereof into said opening.

19. The chamber of claim 18, wherein said closure element is situated at a distance from said end opening which distance is less than twice a diameter of said end opening.

20. The chamber of claim 2, wherein said connection port exhibits an end opening, and wherein said closure element is arranged internally of said connection port and is distanced from said end opening.

21. The chamber of claim 20, wherein said distance is greater than half a diameter of said end opening.

22. The chamber of claim 20, wherein between said closure element and said end opening, said connection port exhibits an internal surface having at least a sealing part which is destined to seal with said external element, said sealing part having a decreasing section in a direction departing from said end opening and going towards said closure element.

23. The chamber of claim 2, comprising, apart from said access port, at least a second access port and a third access port.

24. The chamber of claim 23, wherein said second access port is a blood inlet port and said third access port is a blood outlet port.

25. The chamber of claim 2, wherein said access port is a service port predisposed for fluid connection with a device for detecting a pressure, said device being associated to a machine for extracorporeal blood treatment.

26. The chamber of claim 2, wherein between said first end and said second end said connection line is provided with a transducer-protector device having an anti-contamination barrier which is permeable to gas.

27. The chamber of claim 2, wherein said connection line is a service line of said extracorporeal circuit.

28. An extracorporeal circuit comprising at least a blood chamber realised according to claim 2.

29. The connector of claim 1, wherein said closure element is realised in a single piece with said tubular body.

30. The connector of claim 1, wherein said closure element is arranged internally of said tubular body and is distanced from an end opening of said second connection port.

31. The connector of claim 30, wherein an internal surface is predisposed between said closure element and said end opening, which internal surface has a passage section which decreases in a direction departing from said end opening and going towards said closure element.

32. The connector of claim 30, wherein said axial distance is greater than a half of a diameter of said end opening.

33. The connector of claim 1, wherein said fluid passage has a straight axis and wherein said first and second connection ports are coaxial one to another.

34. The connector of claim 1, wherein said closure element is provided with at least one hinge, at least a part of said closure element being able to assume an open configuration in which, with respect to a closed configuration thereof, said at least a part of the closure element is rotated about said at least one hinge.

35. The connector of claim 34, wherein said hinge comprises a localised thickened part of said closure element.

36. The connector of claim 1, wherein said closure element comprises a breakable body.

37. The connector of claim 36, wherein said breakable body exhibits at least a zone predisposed for easy breakage.

38. The connector of claim 37, wherein said at least a zone predisposed for easy breakage comprises one or more weakened lines.

39. The connector of claim 38, wherein said at least a zone predisposed for easy breakage comprises a plurality of weakened lines arranged in a spoke fashion departing from a central zone of said breakable body.

40. The connector of claim 36, wherein said breakable body has a perimeter part which is constrained to said tubular body and a central part which thins gradually towards a centre of said central part.

41. The connector of claim 1, wherein said closure element is a membrane which transversally occludes said fluid passage.

42. The connector of claim 1, wherein said closure element is at least partially openable in an opening direction which is parallel to or coincides with a longitudinal axis of said tubular body.

43. The connector of claim 1, wherein said closure element is arranged transversally to a longitudinal axis of said tubular body.

44. The connector of claim 1, wherein said closure element is made of a same material as said tubular body.

45. The connector of claim 1, wherein said closure element has a perimeter which is solidly connected to an internal wall of said tubular body.

46. The connector of claim 1, wherein said second connection port exhibits an end opening which is predisposed at least partially to receive a projection borne on said external element, said closure element being openable by effect of a contacting thrust exerted by said projection during insertion thereof into said end opening.

47. The connector of claim 46, wherein said closure element is situated at a distance from said end opening which is less than twice a diameter of said end opening.

48. The connector of claim 1, wherein said second connection port exhibits an end opening, and wherein said closure element is arranged internally of said second connection port and is distanced from said end opening.

49. The connector of claim 48, wherein said distance is greater than half of the diameter of said end opening.

50. The connector of claim 1, wherein said closure element can assume an open configuration in which said closure element is arranged between a projection of said external element and an internal surface of said second connection port.

51. A circuit for extracorporeal blood circulation, comprising a plurality of fluid lines, at least one of which is provided with a connector made according to claim 1.

52. The circuit of claim 51, wherein said plurality of fluid lines comprises two or more fluid lines selected from a group comprising:
at least an arterial line, or a blood removal line, having at least a first end which is destined to be connected to a vascular access device, and at least a second end destined to be connected to a blood treatment device;
at least a venous line, or a blood return line, having at least a first end which is destined to be connected to a blood treatment device, and at least a second end which is destined to be connected to a vascular access device; and
at least a service line having at least a first end which is fluidly connected to a blood pathway of the circuit, and at least a second end destined to be fluidly connected to an external element.

53. The connector of claim 1, wherein the connector is configured to connect a service line connected to a blood chamber of an extracorporeal circuit to a device for pressure detection, said device being associated to a machine for extracorporeal blood treatment.

54. The connector of claim 1, wherein the connector is configured to connect an arterial line to a vascular access device and/or to a blood treatment device.

55. The connector of claim 1, wherein the connector is configured to connect a venous line to a blood treatment device and/or to a vascular access device.

56. An apparatus for extracorporeal blood treatment comprising an extracorporeal circuit made according to claim 28.

57. The apparatus of claim 56, which is able to perform one or more of following treatments: hemodialysis, hemofiltration, hemodiafiltration, pure ultrafiltration, and plasmapheresis.

58. The connector of claim 1, wherein the second connection port exhibits a female Luer coupling which is configured to rotatably couple with a male Luer coupling defined by the external element.

59. A machine for performing an extracorporeal blood treatment comprising:
- a pressure sensor;
- an external element fluidly connected to the pressure sensor, the external element being provided with a projection; and
- a connector as claimed in claim 1,
- wherein the projection, in a coupled configuration, at least partially enters the opening of the second connection port.

60. The machine of claim 59, wherein the external element has a Luer coupling.

61. The machine of claim 59, wherein the projection is externally truncoconical.

62. The machine of claim 59, wherein the projection has a truncoconical external surface for fluidly-sealed coupling with an internal surface of the connector.

* * * * *